(12) United States Patent
Lysyansky et al.

(10) Patent No.: US 6,221,020 B1
(45) Date of Patent: Apr. 24, 2001

(54) SYSTEM AND METHOD FOR PROVIDING VARIABLE ULTRASOUND ANALYSES IN A POST-STORAGE MODE

(75) Inventors: Peter Lysyansky, Haifa; Ilan Lifshitz, Zichron Yaqcov; Nahi Halmann; Alex Sokulin, both of Haifa, all of (IL)

(73) Assignee: G.E. Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/298,563

(22) Filed: Apr. 22, 1999

(51) Int. Cl.$^7$ .................................................. A61B 8/02

(52) U.S. Cl. ............................................................ 600/453

(58) Field of Search .................................. 600/449, 450, 600/453, 458, 454, 447; 73/625, 626

(56) References Cited

U.S. PATENT DOCUMENTS

| | | | |
|---|---|---|---|
| 5,544,655 | * | 8/1996 | Daigle .................................. 600/447 |
| 6,039,690 | * | 3/2000 | Holley et al. ........................ 600/440 |
| 6,050,948 | * | 4/2000 | Sasaki et al. ........................ 600/453 |
| 6,068,598 | * | 5/2000 | Pan et al. ............................. 600/453 |

* cited by examiner

Primary Examiner—Marvin M. Lateef
Assistant Examiner—Ali M. Imam
(74) Attorney, Agent, or Firm—McAndrews, Held & Malloy, Ltd.

(57) ABSTRACT

A system and method for accumulating ultrasound information from a region of interest during a storage period are disclosed. The accumulated ultrasound information is then processed during a post-storage operation to provide a number of various and selectable analysis and display modes. Ultrasound echo signal data comprising, for example, a complete set of raw RF signal samples (or the quadrature signals I & Q) are accumulated in a cinescan memory during a storage period for multiple range positions along one or more scan lines covering a region of interest. Line interleaving and multi-line acquisition techniques may be employed in data accumulation. The accumulated echo signal data is processed during a post-storage operation to provide a number of various and selectable analysis and display modes. During the post-storage playback operation, any known signal processing and data manipulation techniques, which have conventionally been carried out in real-time during a scanning session, may be employed. The various known parameters of signal processing and data manipulation may be selectably modified during post-storage playback to optimize the displayed output. For example, in an off-line playback mode, the system operator may select any scan line and Doppler gate location and width within the region of interest for spectral Doppler analysis or for color M-mode analysis. The system operator may also manually set and reset one or more beam/vessel angles during the off-line playback mode to provide quantitative velocity color mapping. Other parameters such as spectrum scale, Doppler dynamic range, Doppler gain, baseline and color mapping may also be modified during off-line playback. Other known signal processing operations such as noise suppression, filtering, low intensity rejection and/or fixed target canceling may be performed, and the parameters thereof adjusted, during the post-storage operation.

37 Claims, 3 Drawing Sheets

SYSTEM AND METHOD FOR PROVIDING VARIABLE ULTRASOUND ANALYSES IN A POST-STORAGE MODE

CROSS-REFERENCE TO RELATED APPLICATIONS

None

STATEMENT REGARDING FEDERALLY SPONSORED RESEARCH OR DEVELOPMENT

Not applicable.

BACKGROUND OF THE INVENTION

The present invention relates to ultrasound systems which image anatomical structures and the movement thereof. More particularly, the present invention relates to a method and apparatus for accumulating and storing a complete set of ultrasound information from a region of interest during a scanning period and then, in a post-scanning operation, processing the stored ultrasound information to provide a number of various and selectable analysis and display modes.

Doppler ultrasound systems rely on the Doppler effect to detect movement by measuring the change in frequency between a transmitted ultrasound signal and the retuning echoes. If it is necessary or desirable to limit Doppler analysis only to echoes returned from a structure at a known depth, pulsed ultrasound is employed. Pulsed ultrasound allows the time for the ultrasound signal to make a round trip from the transmitter to the target and back to the receiver to be measured and the depth of reflecting structures calculated. In pulsed Doppler systems the operator has the opportunity of determining the depth from which Doppler signals are to be collected. In practice this is done by selectively ignoring signals returning to the receiver until a selected time interval after transmission of the ultrasonic pulse. The receiver is then switched on for a further short interval, during which Doppler information is collected. The duration of this collection interval determines the length of the data collection volume within the tissue. The sensitive zone created by this technique is commonly referred to as the "range gate" or "Doppler gate".

Spectral Doppler uses pulsed Doppler techniques to measure the velocity of targets, such as blood cells within a vessel, at a predefined depth. Usually a two-dimensional B-mode ultrasound image is used to locate the vessel of interest. The system operator then sets the Doppler gate to correspond to the location (depth) and width of the vessel along the appropriate ultrasound beam or scan line. Once the Doppler gate is set, a number of clinically useful analyses can be made. For example, spectrum analysis of the Doppler shift frequencies provides information regarding the range of different velocities within a vessel. A blockage or stenosis within a blood vessel, for example, will create a wider range of velocities and, therefore, a broader spectrum of Doppler shift frequencies would be observed than in the case of a healthy vessel. A quantitative velocity analysis can be made if the angle between the ultrasound beam and long axis of the vessel is known. Many conventional ultrasound systems permit the operator to set the beam/vessel angle by tracing a line along the axis of the vessel under examination.

Because of the rapidity and transient nature of abnormal blood flow patterns and other movements such as cardiac contractions, Doppler ultrasound systems may use recording systems to store a series of images. These images may then be played back at slow speed or frame by frame in a post-scanning operation. Video recorders or a digital memory (often referred to as a "cine loop") capable of recording a few seconds worth of images are incorporated into many conventional ultrasound systems. The information stored by and played back from a typical cine loop is generally limited by the analysis being performed during recording. The reason for this limitation is that a conventional cine loop receives data produced after the echo signals have been processed and prepared for display. Therefore, the cine loop stores only the data resulting from a particular processing operation carried out upon the echo signals. The processing operation is determined by the present mode of operation and parameter settings. The processed data may ignore and/or eliminate certain information from the echo signals. For example, if color flow imaging were being performed on one sub-region within a region of interest, the only information that is stored and available for playback may be the same color flow image from the same sub-region. Similarly, post-scanning playback of a spectral Doppler analysis is limited by the Doppler gate location and width set prior to initiating the cine loop recording. Information contained in echoes received outside the Doppler gate "window" or along non-selected scan lines is ignored and, therefore, lost forever. Also, the accuracy and usefulness of a quantitative velocity measurement would depend on the beam/vessel angle traced during the original scan.

The above mentioned limitations of known cine loop schemes lead to several disadvantages. For example, each time a different kind of Doppler analyses is undertaken, a different Doppler gate location or width is set or a different sub-region is selected for color flow imaging, an additional scanning period must be initiated and new information must be stored in the cine loop. Analyses of different structures at multiple gate locations at the same moment in time is not possible. Also, an abnormality recognized in a recorded image after the patient has left, cannot be analyzed in greater detail unless the patient returns for a new scanning session (and then the abnormality present during the original scanning session may not reveal itself). Images that are recorded while inaccurate or less than optimal parameters are set may be useless. Anything that increases the length or number of ultrasound scanning sessions, may increase patient exposure time, patient discomfort and procedure costs. Furthermore, studies employing contrast agents are limited in the number of different analyses that can be performed during the rapid decay of the contrast agent.

A need remains for an improved ultrasound system to overcome the above-identified difficulties and limitations. It is an object of the present invention to meet this need.

SUMMARY OF THE INVENTION

A system and method for accumulating unprocessed ultrasound information from a region of interest during a storage period is provided. The accumulated ultrasound information is then processed during a post-storage operation to provide a number of various and selectable ultrasound movement analysis and display modes.

Ultrasound echo signal data comprising, for example, a complete set of RF signals (or the quadrature signals I & Q) are accumulated in a cinescan memory during a storage period for multiple range positions along a scan line. Line interleaving techniques may be used to simultaneously accumulate ultrasound information from multiple scan lines covering a region of interest. Optimally, the maximum available pulse repetition frequency (PRF) may be used.

Multiple line acquisition (MLA) may be used to increase the size or density of the region of interest from which ultrasound information may be accumulated during the storage period.

The accumulated echo signal data is then processed during a post-storage operation to provide a number of various and selectable ultrasound movement analysis and display modes. During the post-storage playback operation, any known signal processing and data manipulation techniques, which have conventionally been carried out in real-time during a scanning session, may be employed. The various known parameters of signal processing and data manipulation may be selectably modified during post-storage playback to optimize the displayed output. For example, in an off-line playback mode, the system operator may select any scan line and Doppler gate location and width within the region of interest for color M-mode analysis or for spectral Doppler analysis. The system operator may also select any sub-region within the region of interest for color flow or tissue velocity imaging. Other parameters such as spectrum scale, Doppler dynamic range, Doppler gain, baseline and color mapping may also be modified during off-line playback. Other known signal processing operations such as noise suppression, filtering (including wall motion filtering), low intensity rejection and/or fixed target canceling may be performed, and the parameters thereof adjusted, during the post-storage operation.

The ultrasound system according to a preferred embodiment of the present invention may also provide manual beam/vessel angle correction during playback. Beam/vessel angle correction may be employed for a number of imaging modes such as spectral Doppler and color mapping of mean and/or maximum velocity. In the case of color mapping, a quantitative movement analysis is provided by angle correction for one or more vessels within the region of interest.

Other objects, features, and advantages of the present invention will be apparent from the accompanying drawings and from the detailed description that follows below.

DETAILED DESCRIPTION OF THE PREFERRED EMBODIMENT

A method and apparatus are described for accumulating and storing a complete set of ultrasound echo information from a region of interest during a scanning period and then, in a post-storage operation, performing one or more ultrasound movement analyses, such as Doppler analyses, on the stored echo information from a plurality of selectable ultrasound movement analyses. In the following description, numerous specific details are set forth in order to provide a thorough understanding of the preferred embodiment of the present invention. It will be apparent, however, to one of ordinary skill in the art that the present invention may be practiced without these specific details.

Figure 1:
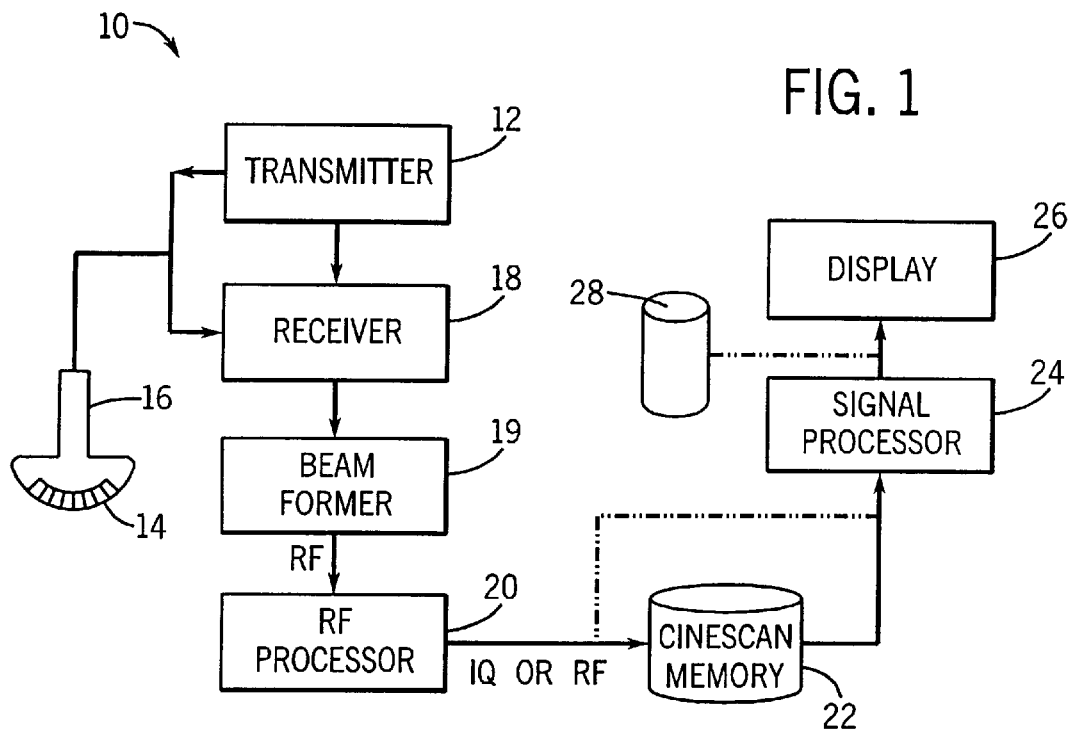
FIG. 1 illustrates a block diagram of an ultrasound imaging system according to a preferred embodiment of the present invention.

A block diagram for an ultrasound system (generally indicated at 10) according to a preferred embodiment of the present invention is shown in FIG. 1. The ultrasound system 10 includes a transmitter 12 which drives transducers 14 within a probe 16 to emit pulsed ultrasonic signals into a body. The ultrasonic signals are backscattered from structures in the body, like blood cells or muscular tissue, to produce echoes which return to the transducers 14. The echoes are detected by a receiver 18. The received echoes are passed through a beamformer 19, which performs beam forming and outputs an RF signal. The RF signal then passes through an RF processor 20. According to a preferred embodiment of the present invention, the RF signal data may then be routed directly to a "cinescan" memory 22 for storage. The term "cinescan" is used to distinguish the cinescan memory 22 from a conventional cine loop memory. Alternatively, the RF processor 20 may include a complex demodulator (not shown) that demodulates the RF signal to form I, Q data pairs representative of the echo signals prior to storage in cinescan memory 22.

Ultrasound system 10 also includes a signal processor 24 to process the received echo signal data (i.e., RF signal data or I, Q data pairs) and prepare an image for display on display 26. The signal processor 24 is adapted to perform one or more processing operations from a plurality of selectable processing operations on the received echo signal data. Echo signal data may be processed and displayed in real-time during a scanning session as the echo signals are received. Additionally or alternatively, according to a preferred embodiment of the present invention, the echo signal data may be stored in cinescan memory 22 during a scanning session and then, in a post-storage (off-line) operation, retrieved from cinescan memory 22, processed by signal processor 24 and displayed on display 26.

Preferably the cinescan memory 22 is of sufficient capacity to store several seconds of echo signal data for multiple range positions along multiple scan lines. The echo signal data is stored in a manner to facilitate retrieval thereof according to scan line, range position and elapsed time from the start of the scanning period. Cinescan memory 22 may comprise any known data storage medium. Cinescan memory 22 may also allow the archiving of echo signal data from multiple scanning sessions and/or multiple patients.

Ultrasound system 10 may also include a conventional cine loop memory 28 for recording displayed images or post-processed echo signal data.

The signal processor 24 may employ any known signal processing and data manipulation techniques to provide any known ultrasound mode or analysis that has conventionally been carried out in real-time during a scanning session. However, these signal processing and data manipulation techniques may be carried out in a post-storage (off-line) operation on stored echo signal data. Furthermore the various known parameters of signal processing and data manipulation may be selectably modified during off-line playback to optimize the displayed output. For example, the operator may select any sub-region within the region of interest for color flow or tissue velocity imaging or any scan line within the region of interest for color M-mode analysis or for spectral Doppler analysis. In the case of spectral Doppler analysis the operator may also select any Doppler gate location and width along the scan lines within the region of interest. Also signal processing operations such as noise suppression, filtering (including wall motion filtering), low intensity rejection and/or fixed target canceling may be performed, and the parameters thereof adjusted, during the post-storage operation. Parameters such as spectrum scale, Doppler dynamic range, Doppler gain, baseline and color mapping may also be modified during off-line playback.

The ultrasound system according to a preferred embodiment of the present invention may also provide manual beam/vessel angle correction during playback. Beam/vessel angle correction may be employed for a number of imaging modes such as spectral Doppler and color mapping of mean and/or maximum velocity. In the case of color mapping, the operator may manually set the beam/vessel angle by tracing a line along the vessel axis while viewing a two-dimensional B-mode image or a qualitative color map of the region of interest. A single angle may be set or multiple angles may be set for multiple vessels within the region of interest. The angles may be set and reset during playback. The system operator is provided with the ability to select a desired vessel, select a desired Doppler gate location and width and to perform manual angle correction off-line. Angle correction may also be performed automatically in any known manner while the off-line playback mode.

Figure 2A:
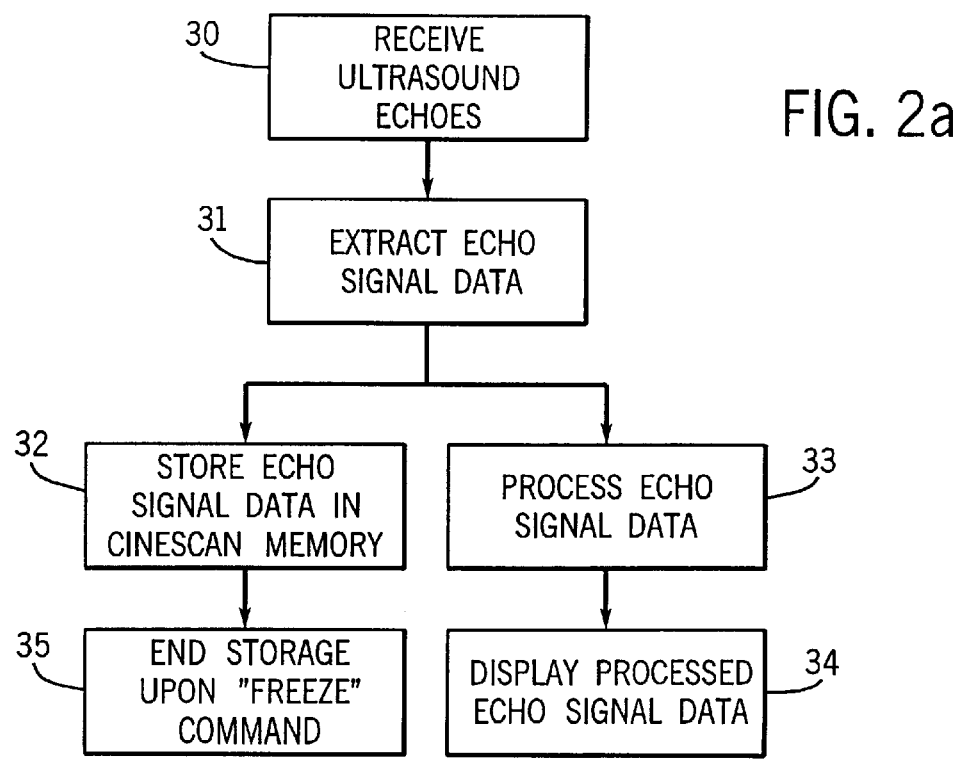
FIGS. 2a and 2b illustrate a flow chart of a procedure for accumulating and storing ultrasound information according to a preferred embodiment of the present invention.
Figure 2B:
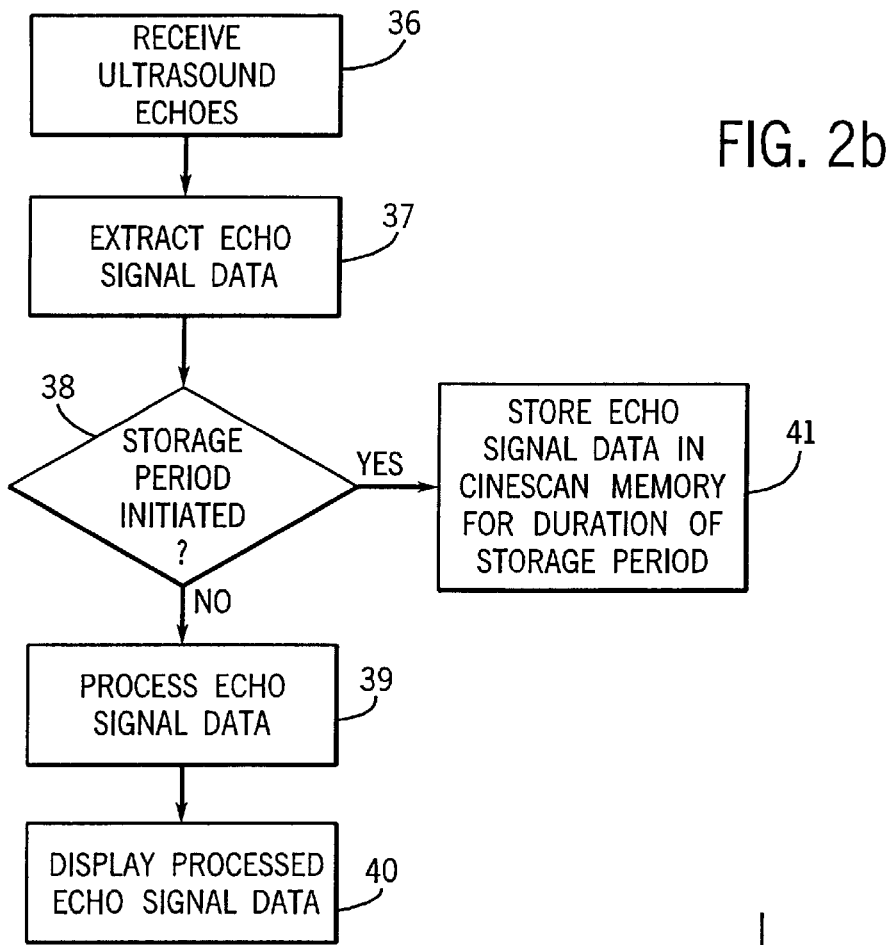

According to a preferred embodiment of the present invention, the storage of echo signal data in cinescan memory 22 may take place continuously when storage is initiated by the system operator. In this case, cinescan memory 22 may be a cyclic memory storing N seconds of data in a first-in-first-out routine. As illustrated in FIG. 2b, the ultrasound system 10 receives ultrasound echoes (step 30) and the RF processor extracts echo signal data (step 31). The echo signal data may comprise, for example, raw RF signal data or I, Q data pairs. The echo signal data is routed to and stored in cinescan memory 22 (step 32). The echo signal data is simultaneously routed to the signal processor 24 for real-time (as opposed to-post storage) processing (step 33) and display on display 26 (step 34) according to the current system parameter settings. An operator initiated command, such as a freeze command, may be used to end the storage period and "lock-in" the immediately previous N seconds of data for off-line playback and/or archiving (step 35).

FIG. 2b illustrates a flow chart of an alternative process for accumulation and storage of echo signal data according to a preferred embodiment of the present invention. The ultrasound system 10 receives ultrasound echoes (step 36) and the RF processor extracts echo signal data (step 37). The echo signal data may comprise, for example, raw RF signal data or I, Q data pairs. If a cinescan storage period is initiated (step 38), the echo signal data is routed to and stored in cinescan memory 22 (step 39). The echo signal data is stored over a predetermined period of time of any length (only limited by the capacity of cinescan memory 22). During this storage period, the probe 16 is held stationary over the region of interest. Upon completion of the storage period, the ultrasound system 10 may return to a real-time processing operation or may prompt the operator to select an off-line playback mode and related parameters. If a cinescan storage period has not been initiated (step 38), the echo signal data is processed in real-time by signal processor 24 (step 40) and then displayed on display 26 (step 41). Although not shown in FIG. 2, real-time (as opposed to post-storage) processing and display of echo signal data may proceed in parallel with the storage of echo signal data in cinescan memory 22.

Alternatively, data may be collected serially from a number of segments of a region of interest during a storage period. In this manner, the storage period comprises a number of storage periods. During the first storage period, data from a first segment is stored. During a second storage period that may commence immediately following the first storage period, data from a second segment that may share a border with the first segment is stored. Further storage periods and segments may be similarly implemented. In this manner, data from a larger region of interest may be collected during a storage period. The number of segments may be increased or decreased to alter the area covered by the region of interest. While a composite image of the segments will represent data stored at different points in time, the image will still provide clinically useful information due to the cyclical or repetitive nature of most anatomical movements.

Figure 3:
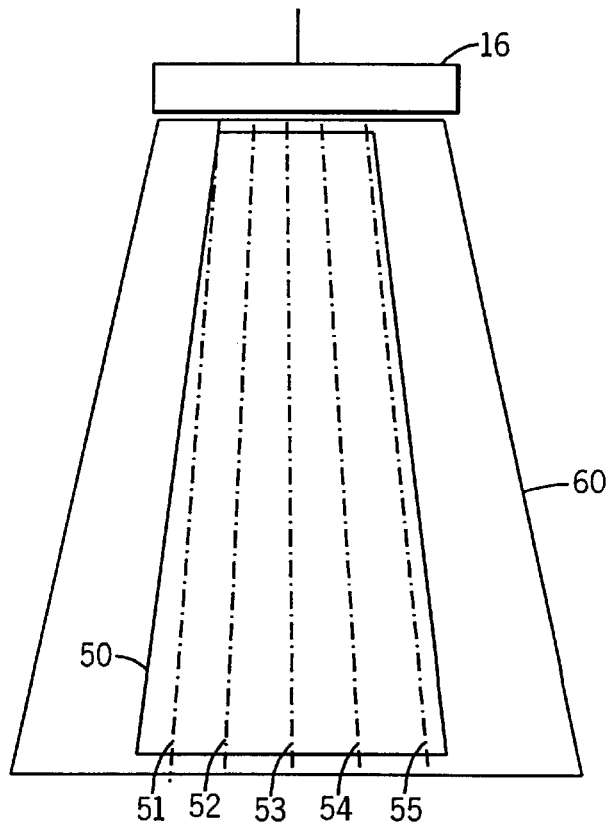
FIG. 3 illustrates a schematic diagram of the accumulation of ultrasound information from a region of interest according to a preferred embodiment of the present invention.

An example of the accumulation and storage of echo signal data from a region of interest is described with respect to FIG. 3. As illustrated in FIG. 3, the region of interest 50 may comprise five scan lines 51, 52, 53, 54 and 55 of a sector scan 60. After a storage period is initiated, the probe 16 is held over the region of interest 50 for the duration of the storage period. For illustrative purposes, the storage period of this example is 6 seconds. During this storage period, echo signal data is accumulated from the scan lines 51, 52, 53, 54 and 55 at a PRF of, for example, 10,000. If an interleave size of five is used and the number of samples per vector is 100, then the number of echo signal data samples stored for each line is 1,200,000. A total of 6,000,000 for the full region of interest. The echo signal data may be stored in a data table according to the scan line from which the echo signal data was collected. The echo signal data may also be indexed according to range position and/or elapsed time from the beginning of the storage period. P The size of the region of interest 50 may be changed by increasing or decreasing the number of scan lines from which data will be accumulated and stored. Line interleaving techniques may be used to allow simultaneous accumulation of echo signal data from multiple lines. The concept of line interleaving refers to an ultrasound firing sequence, in which a group of several lines is repeatedly scanned. Line interleaving can be used when the required minimum PRF (from a clinical view-point—determined by the required velocity range that is to be detected without aliasing) is smaller than the maximum PRF (determined by the depth of the scan). In this case the "dead" time between consecutive firings along one scan line is used to fire along other scan lines. According to a preferred embodiment of the present invention, this concept is employed during the storage period to continuously acquire multiple lines of echo signal data in a region of interest 50 defined by the interleaving size (number of interleaved lines).

The size of the region of interest 50 may be further increased by applying multi-line acquisition MLA). This technique allows reception of more than one receiver beam for each transmitted pulse. Using this technique, a broader ultrasonic beam is transmitted, and the beam-former of receiver 18 is set up to receive and separate the signals from two or more different beam directions within the transmit beam opening angle. Use of a broader ultrasonic beam allows the accumulation of echo signal data from a larger region of interest than could be covered without the use of MLA.

Figure 4:
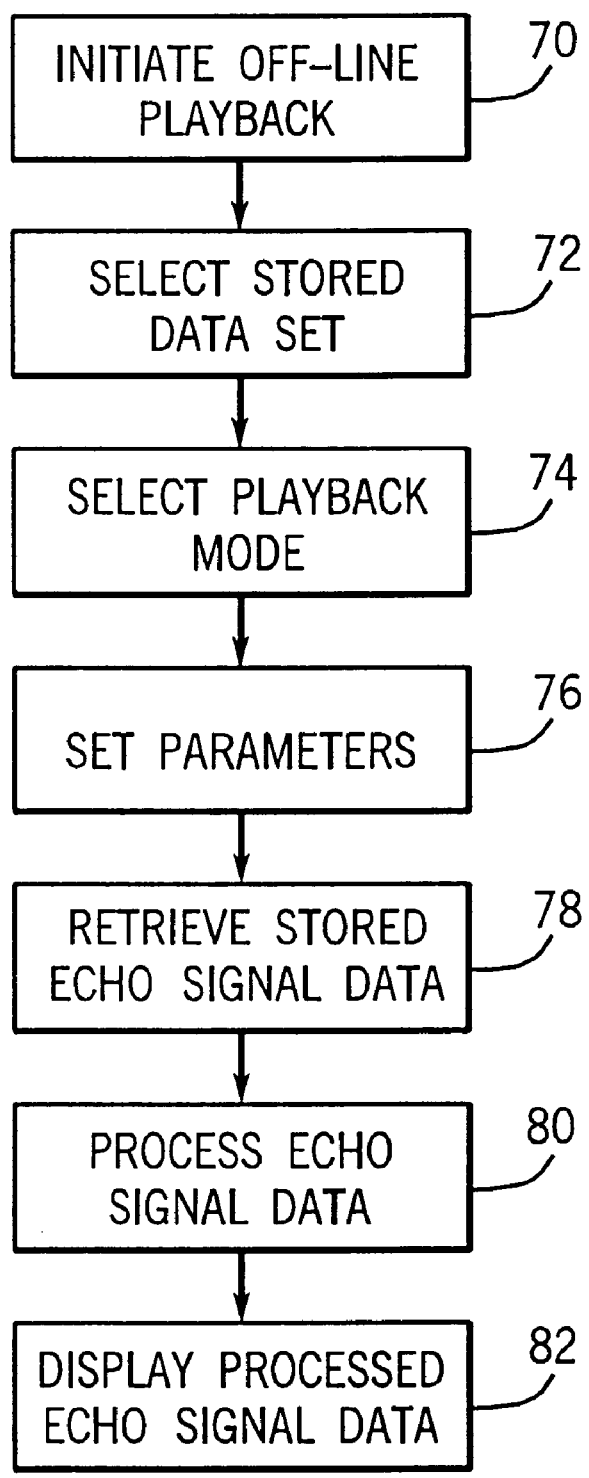
FIG. 4 illustrates a flow chart of a procedure for processing the stored ultrasound information, in a post-storage mode, to provide a number of various and selectable ultrasound movement analyses according to a preferred embodiment of the present invention.

FIG. 4 illustrates a flow chart of a post-storage, off-line playback operation that may be carried out by the ultrasound system 10 for processing the stored echo signal data. Playback may take place on the same ultrasound system as was used to accumulate and store the data set, another ultrasound system, or a separate workstation. At step 70, the off-line playback mode is initiated by the operator. At this point, the operator may be prompted to select an archived data set or the most recently stored data set for playback (step 72). Next, the playback mode or analysis is selected (step 74).

The playback modes or analyses selected at step 74 of FIG. 4 may include, for example: standard Doppler analyses such spectral Doppler including Doppler Audio playback, color flow, tissue velocity imaging and/or color M mode; advanced Doppler color mapping analyses such as maximum velocity color mapping, pulsatility index color mapping, resistive index color mapping, spectral Doppler derivatives and/or statistical flow parameters; tailored clinical studies such as cartiod, renal, malignant neovascularization, feto placental and/or coronaries studies; and/or other advanced studies such as contrast agents and/or tissue elasticity studies. Some of the playback modes may take advantage of the fact that a complete data set for the entire region of interest and the entire storage period is available simultaneously. Also, for playback modes requiring intensive data processing that are difficult or impossible to accomplish in an on-line real-time operation due to processing limitations, processing may be performed on the stored data set without the speed requirements of real-time processing and display.

At step 76, the various parameters of the selected playback mode or analysis are set. To facilitate the selection of such parameters as M-mode scan line, Doppler gate location and width and/or setting of beam/vessel angle, the ultrasound system 10 may be a duplex scanner that stores B-mode image information from the region of interest 50 during the storage period. A B-mode image of the region of interest 50 is then displayed during the post-storage playback operation. The operator may use this B-mode image to locate vessels and set parameters accordingly. All of the available parameters may be set and reset before or during the post-storage playback operation.

The signal processor 24 then retrieves the portion of the stored echo signal data from the cinescan memory 22 that is appropriate for the selected mode and parameters (step 78). The retrieved echo signal data is then processed by signal processor 24 (step 80) and displayed on the display 26 (step 82).

The stored echo signal data may be processed and displayed an unlimited number of times according to any of the available processing modes and parameter settings. For example, the echo signal data may first be processed and displayed according to a spectral Doppler mode and then, later, be processed and displayed according to a color mapping mode and/or M-mode. Also, for example, spectral Doppler may first be performed for one scan line, Doppler gate location, and Doppler gate width and then, later, spectral Doppler may be performed for a different scan line, Doppler gate location and/or Doppler gate width.

In the foregoing specification the invention has been described with reference to specific exemplary embodiments thereof It will, however, be evident that various modifications and changes may be made thereto without departing from the broader spirit and scope of the invention as set forth in the appended claims. The specification and drawings are, accordingly, to be regarding in an illustrative rather than restrictive sense.

What is claimed is:

1. A method of analyzing movement of anatomical structures within a region of interest comprising:

receiving ultrasound echoes from a plurality of range positions along at least one scan line within said region of interest;

storing said echo signal data representative of the received echoes during a storage period;

processing the stored echo signal data during a post-storage period; and displaying an image representative of the processed echo signal data.

2. The method according to claim 1, wherein complex demodulation is performed on the received echoes to produce said echo signal data.

3. The method according to claim 1, wherein no substantial filtering of echoes or echo signal data occurs before storing.

4. The method according to claim 1, wherein ultrasound echoes are received, and echo signal data is extracted and stored, for all possible Doppler gate locations along said scan line within said region of interest.

5. The method according to claim 1, wherein ultrasound echoes are received and echo signal data is stored for multiple range positions along at least two scan lines covering said region of interest.

6. The method according to claim 5, wherein line interleaving techniques are used to receive ultrasound echoes from said at least two scan lines.

7. The method according to claim 6, wherein multi-line acquisition techniques are used to receive ultrasound echoes from said at least two scan lines.

8. The method according to claim 5, further comprising selecting one of said at least two scan lines during the post-storage period for color M-mode display.

9. The method according to claim 1, further comprising:

receiving ultrasound echoes from a plurality of range positions along at least one further scan line within said region of interest; and storing said echo signal data representative of the received echoes during a further storage period.

10. The method according to claim 1, further comprising setting a Doppler gate location and width during the post-storage period.

11. The method according to claim 1, further comprising setting a beam/vessel angle during the post-storage period.

12. The method according to claim 1, further comprising storing the processed echo signal data in a conventional cine loop.

13. A Doppler ultrasound imaging system analyzing movement of anatomical structures within a region of interest comprising:

a receiver receiving ultrasound echoes from a plurality of range positions along at least one scan line covering said region of interest;

an RF processor extracting echo signal data from said echoes;

a memory storing said echo signal data during a storage period;

a signal processor processing the stored echo signal data during a post-storage period; and a display displaying the processed echo signal data.

14. The Doppler ultrasound imaging system according to claim 13, wherein the RF processor includes a complex demodulator for performing complex demodulation on said echoes.

15. The Doppler ultrasound imaging system according to claim 13, wherein the RF processor does not include a filter.

16. The Doppler ultrasound imaging system according to claim 13, wherein the memory stores echo signal data for all possible Doppler gate locations along said scan line within said region of interest.

17. The Doppler ultrasound imaging system according to claim 13, wherein the receiver receives echoes, and the memory stores echo signal data, for multiple range positions along at least two scan lines covering said region of interest.

18. The Doppler ultrasound imaging system according to claim 17, wherein the receiver and RF processor use line interleaving techniques to receive ultrasound echoes from said at least two scan lines.

19. The Doppler ultrasound imaging system according to claim 18, wherein the receiver and RF processor use multi-line acquisition techniques to receive ultrasound echoes from said at least two scan lines.

20. The Doppler ultrasound imaging system according to claim 17 wherein the signal processor allows the selection of one of said at least two scan lines during the post-storage period for color M-mode display.

21. The Doppler ultrasound imaging system according to claim 13, further comprising a Doppler gate selector operable to set a Doppler gate location and width during the post-storage period.

22. The Doppler ultrasound imaging system according to claim 13, further comprising a beam/vessel angle selector operable to set a beam/vessel angle during the post-storage period.

23. The Doppler ultrasound imaging system according to claim 13, further comprising a conventional cine loop memory for storing the processed echo signal data.

24. A method of analyzing movement of anatomical structures within a region of interest comprising:

receiving ultrasound echoes from said region of interest;

storing echo signal data representative of said echoes during a storage period;

processing and displaying the stored echo signal data according to a first processing mode of a plurality of processing modes during a first processing period; and processing and displaying the stored echo signal data according to a second processing mode of a plurality of processing modes during a second processing period, wherein said storage period, said first processing period and said second processing period do not overlap in time.

25. The method according to claim 24, wherein ultrasound echoes are received, and echo signal data is stored for a plurality of range positions along at least one scan line covering said region of interest.

26. The method according to claim 25, wherein ultrasound echoes are received, and echo signal data is stored, for all possible Doppler gate locations along said scan line within said region of interest.

27. The method according to claim 24, wherein ultrasound echoes are received, and echo signal data is stored, for multiple range positions along at least two scan lines covering said region of interest.

28. The method according to claim 24, wherein the first processing mode includes processing echo signal data associated with one of said at least two scan lines and the second processing mode includes processing echo signal data for another of said at least two scan lines.

29. The method according to claim 24 wherein ultrasound echoes are received from a first segment of said region of interest during a first storage period and ultrasound echoes are received from a second segment of said region of interest during a second storage period.

30. The method according to claim 24, wherein the first processing mode includes processing echo signal data for a first Doppler gate location and the second processing mode includes processing echo signal data for a second Doppler gate location.

31. The method according to claim 24, wherein the first processing mode includes processing echo signal data for a first Doppler gate width and the second processing mode includes processing echo signal data for a second Doppler gate width.

32. The method according to claim 24, wherein the first processing mode includes processing a portion of the echo signal for at least one beam/vessel angle and the second processing mode includes processing a portion of the echo signal data for at least one different beam/vessel angle.

33. The method according to claim 24, wherein one of said first and second processing modes is a spectral Doppler mode and the other of said first and second processing modes is a color mapping mode.

34. The method according to claim 24, wherein one of said first and second processing modes is a spectral Doppler mode and the other of said first and second processing modes is an M-mode.

35. The method according to claim 24, wherein one of said first and second processing modes is a color mapping mode and the other of said first and second processing modes is an M-mode.

36. The method according to claim 24, wherein one of said first and second processing modes is a mean velocity color mapping mode and the other of said first and second processing modes is a maximum velocity color mapping mode.

37. The method according to claim 24, wherein one of said first and second processing modes is a qualitative color mapping mode and the other of said first and second processing modes is a quantitative color mapping mode.

* * * * *